US008247624B2

(12) United States Patent
Merkel et al.

(10) Patent No.: US 8,247,624 B2
(45) Date of Patent: *Aug. 21, 2012

(54) PROCESS FOR PRODUCING FLUOROPROPENES

(75) Inventors: Daniel C. Merkel, Orchard Park, NY (US); Rajiv R. Singh, Getzville, NY (US); Hsueh S. Tung, Getzville, NY (US)

(73) Assignee: Honeywell International Inc., Morristown, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 13/226,019

(22) Filed: Sep. 6, 2011

(65) Prior Publication Data
US 2012/0053370 A1    Mar. 1, 2012

Related U.S. Application Data

(63) Continuation of application No. 12/887,739, filed on Sep. 22, 2010, now Pat. No. 8,034,984, which is a continuation of application No. 12/104,176, filed on Apr. 16, 2008, now Pat. No. 7,803,973, which is a continuation of application No. 11/757,782, filed on Jun. 4, 2007, now abandoned, which is a continuation of application No. 10/694,272, filed on Oct. 27, 2003, now Pat. No. 7,230,146.

(51) Int. Cl.
*C07C 17/00* (2006.01)
(52) U.S. Cl. ......... 570/156; 570/157; 570/167; 570/168
(58) Field of Classification Search .................. 570/156, 570/157, 167, 168
See application file for complete search history.

(56) References Cited

U.S. PATENT DOCUMENTS

| | | | |
|---|---|---|---|
| 2,889,379 A | 6/1959 | Ruh et al. | |
| 2,996,555 A | 8/1961 | Rausch et al. | |
| 3,472,826 A | 10/1969 | Potts et al. | |
| 3,659,023 A | 4/1972 | Regan | |
| 4,465,786 A | 8/1984 | Zimmer et al. | |
| 4,650,914 A | 3/1987 | Woodard | |
| 4,798,818 A | 1/1989 | Baizer et al. | |
| 4,900,874 A | 2/1990 | Ihara et al. | |
| 5,155,082 A | 10/1992 | Tung et al. | |
| 5,532,419 A | 7/1996 | Van Der Puy et al. | |
| 5,545,777 A | 8/1996 | Morikawa et al. | |
| 5,574,192 A | 11/1996 | VanDerPuy et al. | |
| 5,679,875 A | 10/1997 | Aoyama et al. | |
| 5,710,352 A | 1/1998 | Tung | |
| 5,728,904 A | 3/1998 | Van Der Puy et al. | |
| 5,969,198 A | 10/1999 | Thenappan et al. | |
| 5,986,151 A | 11/1999 | Van Der Puy | |
| 6,023,004 A | 2/2000 | Thenappan et al. | |
| 6,031,141 A | 2/2000 | Mallikarjuna et al. | |
| 6,111,150 A | 8/2000 | Sakyu et al. | |
| 6,124,510 A | 9/2000 | Elsheikh et al. | |
| 6,369,284 B1 | 4/2002 | Nappa et al. | |
| 6,548,719 B1 | 4/2003 | Nair et al. | |
| 6,809,226 B1 | 10/2004 | Pennetreau et al. | |
| 6,958,424 B1 | 10/2005 | Nair et al. | |
| 7,230,146 B2 | 6/2007 | Merkel et al. | |
| 7,592,494 B2 | 9/2009 | Tung et al. | |
| 7,803,973 B2 | 9/2010 | Merkel et al. | |
| 7,829,748 B1 | 11/2010 | Tung et al. | |
| 2005/0020862 A1 | 1/2005 | Tung et al. | |
| 2005/0090698 A1 | 4/2005 | Merkel et al. | |
| 2005/0171391 A1 | 8/2005 | Janssens et al. | |

FOREIGN PATENT DOCUMENTS

| | | |
|---|---|---|
| EP | 0522639 A1 | 1/1993 |
| EP | 0644173 A1 | 3/1995 |
| EP | 0974571 A2 | 1/2000 |
| JP | 10007604 A | 1/1998 |
| JP | 11-140002 A | 5/1999 |
| JP | 2000169404 A | 6/2000 |
| WO | 9504021 A1 | 2/1995 |
| WO | 9601797 A1 | 1/1996 |
| WO | 9833755 A1 | 8/1998 |
| WO | 2005012212 A2 | 2/2005 |
| WO | 2005042451 A2 | 5/2005 |

OTHER PUBLICATIONS

Knunyants, I.L. et al.., "Reactions of Fluoro Olefins. Communication 13. Catalytic Hydrogenation of Perfluoro Olefins," Bulletin of Academy of Sciences of the USSR, Div. of Chemical Sciences, pp. 1312-1317 (1960) XP000578879 RU.

Kunshanko, B.V. et al., "Reaction of Organic Compounds with SF4-HF-Halogenating System . . . ," Journal of Organic Chemistry of the USSR (translation of Zhurnal Organischekoi Khimii), vol. 28, No. 4, Part 1, pp. 511-518 (Apr. 1992) English Translation. RU.

Haszeldine, R.N. et al., "Free Radical Additions to Unsaturated Systems. Part XVII. Reaction of Trifluoroiodomethane with Mixtures of Ethylene and Vinyl Fluoride and of Ethylene and Propene," Journal of Chemical Society, Section C: Organic, vol. 3, pp. 414-421 (1970) XP002343900 GB.

Henne et al., "Fluorinated Derivatives of Propane and Propylene. VI," Journal of American Chemical Society, vol. 68, pp. 496-497 (1946) US.

Tarrant et al., "Free Radical Additions Involving Fluorine Compounds. IV. The Addition of Debromodifluoromethane to Some Fluoroolefins," Journal of American Chemical Society, vol. 77, pp. 2783-2786 (1955) US.

Kimura et al., "Poly(ethylene glycols) and Poly(ethylene glocol)-Grafted Copolymers are Extraordinary Catalysts for Dehydrohalogenation Under Two-Phase and Three-Phase Conditions," J. Organic Chemistry, vol. 48, pp. 195-198 (1983) US.

Database WPI, Section CH, Week 199931, Derwent Publications Ltd., London, GB; AN 1999-367023, XP002324079 (Nov. 11, 1997) GB.

PCT Search Report Form PCT/ISA/206 for PCT/US04/35131, Filed Oct. 25, 2004. WO.

*Primary Examiner* — Sikarl Witherspoon
(74) *Attorney, Agent, or Firm* — Bruce O. Bradford

(57) ABSTRACT

Dehydrohalogenation processes for the preparation of fluoropropenes from corresponding halopropanes, in which the fluoropropenes have the formula $CF_3CY=CX_NH_P$, wherein X and Y are independently hydrogen or a halogen selected from fluorine, chlorine, bromine and iodine; and N and P are independently integers equal to 0, 1 or 2, provided that (N+P)=2.

32 Claims, No Drawings

PROCESS FOR PRODUCING FLUOROPROPENES

RELATED APPLICATIONS

The present application is related to and claims priority benefit of the following U.S. Applications, each of which is also incorporated herein by reference. The present application is a continuation of U.S. application Ser. No. 12/887,739, filed Sep. 22, 2010 (now pending), which in turn is a continuation of U.S. application Ser. No. 12/104,176, filed Apr. 16, 2008 (now U.S. Pat. No. 7,803,973), which in turn is a continuation of U.S. application Ser. No. 11/757,782, filed Jun. 4, 2007 (now abandoned), which in turn is a continuation of U.S. application Ser. No. 10/694,272, filed Oct. 27, 2003 (now U.S. Pat. No. 7,230,146).

BACKGROUND OF THE INVENTION

The present invention relates to a process for producing fluoropropenes in good yield on an industrial scale using commercially and readily available starting materials. More particularly, the present invention relates to a process for producing fluoropropenes by the dehydrohalogenation of halo-propanes, either by reaction with an essentially miscible alkali or alkaline earth metal hydroxide solution in a non-alcohol solvent, or by thermal decomposition.

The production of fluoropropenes such as $CF_3CH=CH_2$ by catalytic vapor phase fluorination of various saturated and unsaturated halogen-containing $C_3$ compounds is described in U.S. Pat. Nos. 2,889,379; 4,798,818 and 4,465,786. U.S. Pat. No. 5,532,419 discloses a vapor phase catalytic process for the preparation of fluoroalkene using a chloro- or bromo-halofluorocarbon and HF. EP 974,571 discloses the preparation of 1,1,1,3-tetrafluoropropene by contacting 1,1,1,3,3-pentafluoropropane (HFC-245fa) in the vapor phase with a chromium-based catalyst at elevated temperature, or in the liquid phase with an alcoholic solution of KOH, NaOH, $Ca(OH)_2$ or $Mg(OH)_2$.

A fluoropropene of particular interest is 1,3,3,3-tetrafluoropropene (HFC-1234ze), which has potential use as a low global warming potential refrigerant. However, this material is presently not available in commercial quantity. The existing technology to make HFC-1234ze is a fluorination process using 1,1,1,3,3-pentachloropropane (HCC-240fa) and HF in the presence of a vapor phase catalyst. HFC-1234ze is a by-product of the reaction that is made in relatively small quantity, i.e., less than about 8 area % in a gas chromatograph (GC) of the organic reaction product.

The process is very expensive because of the low selectivity for the desired product, HFC-1234ze. The reaction is actually intended for the manufacture of HFC-245fa, in which small quantities of HFC-1234ze is produced as a by-product. Complicating matters, the process involves handling large quantities of hazardous materials such as HF and HCl.

Henne et al., *J. Am. Chem. Soc.*, 68, 496-497 (1946) described the synthesis of various fluoropropenes from $CF_3CH_2CF_3$ using, e.g., alcoholic KOH, with varying degrees of success. For example, it is stated that in some instances dehydrohalogenation was unsuccessful. In another instance, a protracted reaction time (3 days) was required, or relatively low product yield (40%, 65%) was obtained.

Tarrant, et al., *J. Am. Chem. Soc.*, 77, 2783-2786 (1955) described the synthesis of $CF_3CH=CF_2$ starting with: (1) 3-bromo-1,1,3,3-pentafluoropropane and reacting it with a hot solution of KOH in water; and (2) 3-bromo-1,1,3,3-tetrafluoropropene, reacting it with HF at 150 C and neutralizing the reaction products with a KOH solution.

Kimura, et al., *J. Org. Chem.* 48, 195-198 (1983) described multi-phase dehydrohalogenation of brominated compounds using aqueous KOH and a phase transfer catalyst based on polyethylene glycols and polyethylene glycol-grafted copolymers. The preparation of fluoropropenes by the dehydrohalogenation of fluoropropane using aqueous KOH and a phase transfer catalyst, but with improved yields and selectivity is disclosed by U.S. Pat. No. 6,548,719.

There is a continuing need for means by which fluoropropenes can be produced commercially with high yield and selectivity, either catalytically or non-catalytically.

SUMMARY OF THE INVENTION

The present invention provides two new dehydrohalogenation methods by which fluoropropenes may be commercially produced with high yield and selectivity. According to one aspect of the present invention, a dehydrohalogenation process is provided for the preparation of fluoropropenes of the formula $CF_3CY=CX_NH_P$, wherein X and Y are independently hydrogen or a halogen selected from the fluorine, chlorine, bromine and iodine, and N and P are independently integers equal to 0, 1 or 2, provided that (N+P)=2, in which there is reacted, without a catalyst, a halopropane of the formula:

$$CF_3C(YR_1)C(X_NH_PR_2)$$

wherein $R_1$, $R_2$, X and Y are independently hydrogen or a halogen selected from fluorine, chlorine, bromine and iodine, provided that at least one of $R_1$, $R_2$, X and Y is a halogen and there is at least one hydrogen and one halogen on adjacent carbon atoms; with a solution of at least one alkali or alkaline earth metal hydroxide in a non-aqueous, non-alcohol solvent therefor that is at least essentially miscible with the halopropane, wherein the reaction is performed at a temperature at which dehydrohalogenation will occur.

Reactions performed without a catalyst produce cleaner reaction products, thereby simplifying product work-up and isolation. The halopropane can be $CF_3CH_2CF_2H$ (a commercially available compound also known as HFC-245fa) or $CF_3CH_2CHClF$ (HCFC-244fa) a by-product of the manufacture of HFC-245fa. Both halopropanes will dehydrohalogenate to form HFC-1234ze.

According to another aspect of the present invention, a dehydrohalogenation process is provided for the preparation of fluoropropenes of the formula $CF_3CY=CX_NH_P$, wherein X and Y are independently hydrogen or a halogen selected from fluorine, chlorine, bromine and iodine, and N and P are independently integers equal to 0, 1 or 2 provided that (N+P)=2, comprising heating to a temperature at which dehydrohalogenation by thermal decomposition occurs a halopropane of the formula:

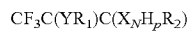
$$CF_3C(YR_1)C(X_NH_PR_2)$$

wherein $R_1$, $R_2$, X and Y are independently hydrogen or a halogen selected from fluorine, chlorine, bromine and iodine, provided that at least one of $R_1$, $R_2$, X and Y is a halogen and there is at least one hydrogen and one halogen on adjacent carbon atoms. The thermal decomposition reaction can be performed either with or without a catalyst for hydrogen halide removal, such as transition metal halides and oxides and combination thereof, preferably iron halides, nickel halides, cobalt halides and combinations thereof. HFC-245fa and $CF_3CH_2CHClF$ (HCFC-244fa) can also be reacted by the thermal decomposition reaction of the present invention to form HFC-1234ze.

DETAILED DESCRIPTION OF THE INVENTION

The present invention can be generally described as a process for the preparation of fluoropropenes of the formula $CF_3CY=CX_NH_p$ wherein X and Y are independently a hydrogen or a halogen selected from fluorine, chlorine, bromine and iodine; and N and P are integers independently equal to 0, 1 or 2, provided that (N+P)=2.

Two dehydrohalogenation methods by which the fluoropropenes may be prepared are disclosed. Both methods dehydrohalogenate a halopropane having the formula:

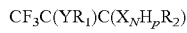

wherein $R_1$, $R_2$, X and Y are independently hydrogen or a halogen selected from fluorine, chlorine, bromine and iodine, provided that at least one of $R_1$, $R_2$, X and Y is a halogen and there is at least one hydrogen and one halogen on adjacent carbon atoms.

Included among the halopropanes that can be included in the present invention is 1,1,1,3,3-pentafluoropropane or HFC-245fa and 1-chloro-1,3,3,3-tetrafluoropropane or HCFC-244fa. Various methods for producing these materials are described in U.S. Pat. Nos. 5,710,352; 5,969,198; 5,728,904; and 6,023,004. Another method described in U.S. Pat. No. 5,574,192 is said to be economical, amenable to large-scale application and uses readily available raw materials. The process of that patent uses two steps as follows: (1) formation of $CCl_3CH_2CHCl_2$ by the reaction of $CCl_4$ with vinyl chloride; and (2) conversion of $CCl_3CH_2CHCl_2$ to $CF_3CH_2CHF_2$ and $CF_3CH_2CHFCl$ by reaction with HF in the presence of a fluorination catalyst selected from antimony halides, niobium halides, arsenic halides, tantalum halides; tin halides; titanium halides; antimony mixed halides; niobium mixed halides, arsenic mixed halides, tantalum mixed halides, mixed tin halides; mixed titanium halides and mixtures thereof. Under-fluorinated materials, such as $CF_3CH_2CHCl_2$, may be recycled in subsequent runs. The under-fluorinated material $CF_3CH_2CHClF$, or HFC-244fa, can also be used as a starting material in the present invention for producing a fluoropropene. Thus, the above-described process can be utilized to obtain two different starting materials for the process of the present invention.

Furthermore, commercial quantities of $CF_3CH_2CF_2H$ are available from Honeywell International, Inc., Morristown, N.J., for use as the starting material of the present process for direct conversion to the fluoroalkene $CF_3CH=CFH$ by dehydrofluorination according to either process disclosed herein. Other useful starting materials for the production of fluoropropenes and/or fluorohalopropenes include the following: $CF_3CH_2CF_2Br$; $CF_3CH_2CF_2I$; $CF_3CHFCF_2Br$; $CF_3CH_2CH_2Cl$; $CF_3CH_2CH_2Br$; $CF_3CH_2CH_2I$; $CF_3CHBrCF_2Br$; $CF_3CHClCF_2Cl$; $CF_3CH_2CFHCl$; $CF_3CH_2CFHBr$; $CF_3CHClCF_2H$; $CF_3CH_2CCl_3$; $CF_3CH_2CF_3$; and the like.

In another embodiment of the invention, HCFC-244fa and/or HFC-245fa can be prepared by fluorinating 1,1,1,3,3-pentachloropropane(HCC-240fa). In this embodiment, in a preliminary step, the process of the invention involves the formation of HCFC-244fa and/or HFC-245fa by reacting 1,1,1,3,3-pentachloropropane (HCC-240fa) with hydrogen fluoride (HF) in the vapor phase, or the liquid phase, preferably in the presence of a fluorination catalyst as is well known in the art.

The result is a reaction product of one or both of the two products, HCFC-244fa and/or HFC-245fa. In the preferred embodiment of the invention, the HF to HCC-240fa mole ratio preferably ranges from about 2:1 to about 100:1; more preferably from about 4:1 to about 50:1 and most preferably from about 5:1 to about 20:1.

Useful fluorination catalysts include, but are not limited to, transition metal halides, Group IVb and Vb metal halides, and combinations thereof, preferably supported on activated carbon or fluorinated alumina. More specifically, preferred vapor phase fluorination catalysts non-exclusively include $SbCl_5$, $SbCl_3$, $SbF_5$, $TaCl_5$, $SnCl_4$, $NbCl_5$, $TiCl_4$, $MoCl_5$, $Cr_2O_3$, $Cr_2O_3/Al_2O_3$, $Cr_2O_3/AlF_3$, $Cr_2O_3/carbon$, $CoCl_2/Cr_2O_3/Al_2O_3$, $NiCl_2/Cr_2O_3/Al_2O_3$, $CoCl_2/AlF_3$, $NiCl_2/AlF_3$ and mixtures thereof. Preferred liquid phase fluorination catalysts non-exclusively include $SbCl_5$, $SbCl_3$, $SbF_5$, $TaCl_5$, $SnCl_4$, $NbCl_5$, $TiCl_4$, and $MoCl_5$. It is understood that after pre-treatment with HF or during reaction in the presence of HF the above mentioned catalyst will be partially fluorinated. Chromium oxide/aluminum oxide catalysts are described in U.S. Pat. No. 5,155,082 which is incorporated herein by reference. Chromium (III) oxides such as crystalline chromium oxide or amorphous chromium oxide are preferred vapor phase fluorination catalysts with amorphous chromium oxide being the most preferred vapor phase catalyst. Chromium oxide ($Cr_2O_3$) is a commercially available material which may be purchased in a variety of particle sizes. Unsupported $SbCl_5$ and $SbCl_3$ halides are preferred liquid phase catalysts. Both of these liquid phase catalysts are commercially available and well known in the art. Fluorination catalysts having a purity of at least 98% are preferred. The fluorination catalyst is present in an amount sufficient to drive the reaction. The fluorination reaction may be conducted in any suitable fluorination reaction vessel or reactor but it should preferably be constructed from materials which are resistant to the corrosive effects of hydrogen fluoride such as nickel and its alloys, including Hastelloy, Inconel, Incoloy, and Monel or vessels lined with fluoropolymers.

Any water in the hydrogen fluoride (HF) will react with and deactivate the fluorination catalyst. Therefore substantially anhydrous hydrogen fluoride is preferred. By "substantially anhydrous" it is meant that the HF contains less than about 0.05 weight % water and preferably contains less than about 0.02 weight % water. However, one of ordinary skill in the art will appreciate that the presence of water in the HF can be compensated for by increasing the amount of catalyst used.

The liquid phase fluorination of HCC-240fa is preferably conducted at a temperature of from about 50° C. to about and 450° C., more preferably from about 60° C. to about 180° C. and most preferably from about 65° C. and 150° C. Fluorination is preferably conducted at a pressure of from about 50 psig to about 400 psig. The reactor is preferably preheated to the desired fluorination reaction temperature while anhydrous HF is fed to the reactor. The HCC-240fa and HF may be fed to the reactor at the desired temperatures and pressures that are described herein. In a preferred embodiment of the invention, either or both of the HCC-240fa and HF are pre-vaporized or preheated prior to entering the reactor.

When HCC-240fa and HF are reacted in a vapor phase with the fluorination catalyst the HCC-240fa and HF may be fed to the reactor at the desired temperatures and pressures that are described herein. The reactor is preheated to the fluorination reaction temperature while anhydrous HF is fed to the reactor. The HCC-240fa and HF may be fed to the reactor at any convenient temperature and pressure. In a preferred embodiment either or both of the HCC-240fa and HF are pre-vaporized or preheated to a temperature of from about 30° C. to about 300° C. prior to entering the reactor. In another embodiment, the HCC-240fa and HF are vaporized in the reactor.

The HF and HCC-240fa feeds are then adjusted to the desired mole ratio. The HF to HCC-240fa mole ratio preferably ranges from about 2:1 to about 100:1; more preferably from about 4:1 to about 50:1 and most preferably from about 5:1 to about 20:1.

The fluorination reaction is conducted at a preferred temperature ranging from about 80° C. to about 400° C.; more preferably from about 100° C. to about 350° C. and most preferably from about 200° C. to about 330° C. Reactor pressure is not critical and can be superatmospheric, atmospheric or under vacuum. The vacuum pressure can be from about 5 torr to about 760 torr. The reactant vapor is allowed to contact the fluorination catalyst for from about 0.01 to about 240 seconds, more preferably from about 0.1 to about 60 seconds and most preferably from about 0.5 to about 20 seconds.

Usually the process flow of the HCC-240fa and HF is in the down direction through a bed of the catalyst. Before each use, the catalyst is preferably dried, pre-treated and activated. It may also be advantageous to periodically regenerate the catalyst after prolonged use while in place in the reactor. For $Cr_2O_3$, $Cr_2O_3/Al_2O_3$, $Cr_2O_3/AlF_3$, $Cr_2O_3/Carbon$, $CoCl_2/Cr_2O_3/Al_2O_3$, $NiCl_2/Cr_2O_3/Al_2O_3$, $CoCl_2/AlF_3$, $NiCl_2/AlF_3$ catalysts, pre-treatment can be done by heating the catalyst to about 250° C. to about 430° C. in a stream of nitrogen or other inert gas. The catalyst may then be activated by treating it with a stream of HF diluted with a large excess of nitrogen gas in order to obtain high catalyst activity. Regeneration of the catalyst may be accomplished by any means known in the art such as, for example, by passing air or air diluted with nitrogen over the catalyst at temperatures of from about 100° C. to about 400° C., preferably from about 200° C. to about 375° C., for from about 1 hour to about 3 days, depending on the size of the reactor. For $SbCl_5$, $SbCl_3$, $TaCl_5$, $SnCl_4$, $NbCl_5$, $TICl_4$, $MoCl_5$ catalysts, supported on an solid support such as activated carbon, pre-treatment or activation can be done by first heating the catalyst to about 30° C. to 250° C. in a stream of nitrogen or other inert gas. It is then treated with a stream of HF in the absence or presence of an oxidizing agent such as chlorine gas in order to obtain high catalyst activity. In addition, the catalyst may optionally be kept active by co-feeding chlorine to the reactor during reaction.

HCFC-244fa and HFC-245fa may be recovered from the fluorination reaction product mixture comprised of unreacted starting materials and by-products, including HCl, by any means known in the art, such as by scrubbing, extraction, and preferably distillation. For example, the distillation may be preferably conducted in a standard distillation column at a pressure, which is less than about 300 psig, preferably less than about 150 psig and most preferably less than 100 psig. The pressure of the distillation column inherently determines the distillation operating temperature. HCl may be recovered by operating the distillation column at from about −40° C. to about 25° C., preferably from about −40° C. to about −20° C. Single or multiple distillation columns may be used. The distillate portion includes substantially all the HCFC-244fa, HFC-245fa, unreacted HF and HCl produced in the reaction as well as any other impurities. In the preferred embodiment, HCFC-244fa and the HFC-245fa are separated from all other reaction by-products and unreacted HF for further reaction in step (b) described herein. In the preferred embodiment, any HF present may also be recovered and recycled back for subsequent fluorination reactions. 1234ze is formed by the dehydrochlorination of 1-chloro-1,3,3,3-tetrafluoropropane (HCFC-244fa) or the dehydrofluorination of 1,1,1,3,3-pentafluoropropane (HFC-245fa).

According to one method of the present invention, the halopropane is dehydrohalogenated with an alkali metal or alkaline earth metal hydroxide in a non-aqueous, non-alcohol solvent for the alkali metal or alkaline earth metal hydroxide that is at least partially miscible with the halopropane. Alkali metal and alkaline earth metal hydroxides suitable for use in the present invention include, but are not limited to LiOH, KOH, NaOH, CaO, $Ca(OH)_2$, $CaCO_3$, and/or lime stone, and the like. By either method, the dehydrochlorination of HCFC-244fa proceeds as follows:

The dehydrohalogenation is performed within a temperature range at which the halopropane will dehydrohalogenate. According to one aspect of this method, alkali metal or alkalin eearth metal hydroxide pellets are dissolved in the solvent with agitation under otherwise ambient conditions. The halopropane is then bubbled through the alkali metal or alkaline earth metal hydroxide solution as the temperature of the solution is gradually increased by heating. Gradual heating is continued until initiation of dehydrohalogenation is observed, after which the temperature at which dehydrohalogenation initiation occurred is maintained until completion of the process.

In carrying out the process, the molar ratio of alkali metal or alkaline earth metal hydroxide relative to the amount of halopropane is from about 1:1 to about 20:1, preferably from about 1:1 to about 15:1; and more preferably from about 1:1 to about 12:1; for example, from 1:1 to about 10:1. In the preferred embodiment of the invention, the caustic strength of the caustic solution is from about 2 wt % to about 100 wt %, more preferably from about 5 wt % to about 90 wt % and most preferably from about 10 wt % to about 80 wt %. The reaction is preferably conducted at a temperature of from about 20° C. to about 150° C., more preferably from about 30° C. to about 110° C. and most preferably from about 40° C. to about 90° C. The reaction pressure is not critical. The reaction can be conducted at atmospheric pressure, super-atmospheric pressure or under vacuum. The vacuum pressure can be from about 5 torr to about 760 torr. Preferably, the reaction is conducted at atmospheric or super-atmospheric pressure.

The dehydrohalogenation reaction can be accomplished using a solution of at least one alkali metal or alkaline earth metal hydroxide in a non, aqueous, non-alcohol solvent for the alkali metal or alkaline earth metal hydroxide that is essentially miscible with the halopropane. For purposes of the present invention, "essentially miscible" means that an agitated mixture containing 50 wt. % halpropane and 50 wt. % solvent does not separate to form more than one liquid phase over the temperature range at which the dehydrohalogenation will occur, or, if such separation does occur, one of the liquid phases is very small, less than 10 wt. % of the total weight of the blend.

Examples of non-alcohol solvents suitable for use with the present invention include, but not limited to, nitriles such as acetonitrile, ethers such as diethyl ether, tetrahydrofuran and perfluoro-tetrahydrofuran, esters such as methyl acetate and ethyl acetate, amides, ketones, sulfoxides, phosphates, carboxylates, and the like.

The alkali metal or alkaline earth metal hydroxide need not be highly soluble in the solvent. An amount of water, alcohol, or mixture thereof may be added to the solvent for the alkali metal or alkaline earth metal hydroxide in quantities that improve the solubility of the alkali metal or alkaline earth metal hydroxide therein. Embodiments according to this aspect of the present invention will blend a solution of the alkali metal or alkaline earth metal hydroxide in water, alcohol or a mixture of water and alcohol, with the solvent. Typically, the amount of water, alcohol, or water-alcohol blend will not exceed about 50 wt.% of the total quantity of solvent for the alkali metal or alkaline earth metal hydroxide, and preferably will not exceed about 20 wt.%. Alcohols that may be used contain from 1 to 5 carbon atoms, and preferably from 1 to 3 carbon atoms.

Solvents are selected that are at least partially miscible with the alkali metal or alkaline earth metal hydroxide solution, which may be in water, alcohol or a mixture thereof. For purposes of the present invention "partially miscible" means a level of miscibility that permits the solvent to dissolve in the alkali metal or alkaline earth metal hydroxide solution to the extent that the dehydrohalogenation reaction will occur upon contact of the halopropane therewith the blend. A high degree is miscibility is not required in order for the reaction to proceed at the interface of the solvent and alkali metal or alkaline earth metal hydroxide solution. More caustic will dissolve as the amount in solution is depleted by the dehydrohalogenation reaction. The solvent need only be at least about 1%, preferably at least about 5%, and more preferably at least 10% soluble, the alkali metal or alkaline earth metal hydroxide solution on a weight basis.

In an alternate embodiment of the invention, the dehydrochlorination of HCFC-244fa and dehydro-fluorination of HFC-245fa may be done by thermal decomposition in the presence or in the absence of a catalyst. Suitable catalysts include transition metal halides and oxides, supported or bulk. Preferred catalysts include, but not limited to, FeCl$_2$, FeCl$_3$, NiCl$_2$, CoCl$_2$, supported or in bulk. The preferred temperatures for the thermal decomposition are from about 30° C. to about 400° C., more preferably from about 50° C. to about 350° C. and most preferably from about 75° C. to about 300° C. As above, the reaction is preferably conducted at atmospheric pressure, super-atmospheric pressure. Reaction under vacuum is also acceptable. The vacuum pressure can be from about 5 torr to about 760 torr.

The reactions may be conducted in any suitable reactor. Further, the dehydrochlorination of HCFC-244fa and the dehydrofluorination of HFC-245fa may either be conducted simultaneously in the same reactor, or they may first be separated followed by separately dehydrochlorinating HCFC-244fa with the caustic solution or by thermal decomposition and separately dehydrofluorinating HFC-245fa with the caustic solution or by thermal decomposition. The result of this two step process is a high yield of HFC-1234ze.

Therefore, according to preferred embodiments of the invention, the dehydrochlorination of HCFC-244fa and dehydrofluorination of HFC-245fa are accomplished either by thermal decomposition or by reacting these with a strong caustic solution at an elevated temperature. By either method, the dehydrochlorination of HCFC-244fa proceeds as follows:

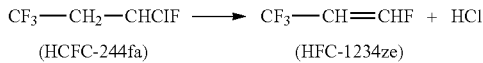

Furthermore, by either method, the dehydrofluorination of HFC-245fa proceeds as follows:

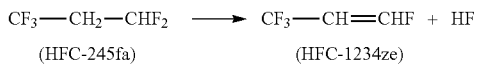

Both the dehydrochlorination of HCFC-244fa and dehydrofluorination of HFC-245fa are achieved according to the present invention by using caustic for hydrogen halide removal or by thermal decomposition in the absence of a catalyst or with a catalyst selected from transition metal halides and oxides and combinations thereof, preferably iron halides, nickel halides, cobalt halides and combinations thereof.

Both processes described herein are useful for the preparation of fluoropropenes and/or fluorohalopropenes having the following formula:

$$CF_3CY=CX_NH_P$$

wherein X and Y and independently hydrogen or a halogen selected from fluorine, chlorine, bromine and iodine; and N and P are integers independently equal to 0, 1 or 2, provided that (N+P)=2. Such compounds include CF$_3$CH=CF$_2$, CF$_3$CH=CFH, CF$_3$CBr=CF$_2$, CF$_3$CH=CH$_2$, CF$_3$CF=CF$_2$, CF$_3$CCl=CF$_2$, CF$_3$CF=CClF, CF$_3$CCl=CHF, CF$_3$CH=CHCl, CF$_3$CCl=CClF, CF$_3$CH=CCl$_2$, CF$_3$CF=CCl$_2$, and the like. The fluoropropenes prepared by both methods of this invention are readily recovered by any means known in the art, such as by scrubbing, extraction, and preferably distillation. Depending on extent of conversion of the starting material, the product can be used directly or further purified by standard distillation techniques. Unreacted halopropane and certain reaction by-products can be recycled back to the reaction vessel to provide a continuous process. Alternatively, fresh halopropane may be supplied to the reaction mixture in order to run the process continuously.

The fluoropropenes obtained by the inventive processes are useful as monomers for producing fluorine-containing oligomers, homopolymers and copolymers, as well as intermediates for other fluorine-containing industrial chemicals.

The following examples are given as specific illustrations of the invention. It should be understood, however, that the invention is not limited to these specific details set forth in the examples. All parts and percentages in the examples, as well as in the remainder of the specification, are by weight unless otherwise specified.

Further, any range of numbers recited in this specification or paragraphs hereinafter describing or claiming various aspects of the invention, such as that representing a particular set of properties, units of measure, conditions, physical states or percentages, is intended to literally incorporate expressly herein by reference or otherwise, any number falling within such range, including any subset of numbers or ranges subsumed within any range so recited. The term "about" when used as a modifier for, or in conjunction with, a variable, is intended to convey that the numbers and ranges disclosed herein are flexible and that practice of the present invention by those skilled in the art using temperatures, concentrations, amounts, contents, carbon numbers, and properties that are outside of the range or different from a single value, will achieve the desired result, namely, processes for the preparation of fluoropropenes and reactants used in such processes.

EXAMPLES

Example 1

To a reaction setup consisting of a 3-neck round bottom flask (5 L), mechanical agitator, reflux condenser, and low temperature cold trap was added to 3000 ml acetonitrile and 9.9 moles (504 g) of KOH pellets. After mixing, 5.1 moles (684 g) of HFC-245fa were added through a dip tube. The reagents were heated slowly with vigorous agitation. Reaction was observed at about 60° C. The crude product was collected in the cold finger. The crude material was analyzed by GC and consisted of a good yield of HFC-1234ze.

Example 2

Example 1 is repeated except 5 moles (752 grams) of HCFC 244fa is added to the acetonitrile/caustic solution through the dip tube. The reagents were heated slowly with vigorous agitation. Reaction is observed at slightly lower temperatures than in Example 1. The crude product is collected in the cold finger. The crude material collected consisted of a good yield of HFC-1234ze.

Example 3

A 50 gal. Fluoropolymer lined reactor was charged with 75 lbs of liquid $SbCl_5$ fluorination catalyst. The reactor was equipped with a 6"D×8'L catalyst stripper containing structured packing and reflux condenser. The catalyst was first fluorinated by adding a sufficient amount of Hydrogen Fluoride (HF). The reactor was heated to 80-95° C. and brought to a pressure of 150-180 psig. Gaseous HF was fed to the reactor continuously at a rate of 23-28 lb/hr through a sparger and liquid 1,1,1,3,3-pentachloropropane (HCC-240fa) was fed continuously at a rate of 40-50 lb/hr. $Cl_2$ was continuously added to the reaction mixture to keep the catalyst active at 1.5-2.0 lb/hr. The gas exiting the reflux condenser was passed through a scrubber that contained KOH solution to remove excess HF and the HCl that was generated during the reaction. Several thousand lbs of the crude product was collected after the scrubber and was analyzed by GC. The following is the analysis of the major component of the crude product in GC area %. Note the presence of the HFC1234ze after the material was passed through the scrubber containing KOH solution.

| Component | GC area % |
|---|---|
| G1234 | 0.1157 |
| 245fa | 92.7560 |
| 1233zd | 0.1269 |
| 244fa | 3.3879 |
| 243fa | 1.6298 |
| Others | 1.9837 |

Example 4

About 132 g (about 1.33 g/cc bulk density) of a chromium (III) oxide catalyst was charged to a reactor of 1" diameter Monel pipe. The catalyst was dried and pretreated with HF before use. The reactor was preheated to the reaction temperature of about 300° C. while anhydrous HF was fed to the reactor. An organic feed (HCC-240) was started when the reactor reached the desired temperature and pressure. The HF and organic feeds were then adjusted to the desired rates. HCFC-244fa and HFC-245fa were found in the reactor effluent product stream, along with other partially fluorinated species such as 1233zd, 1234ze and 243fa.

Example 5

In a typical experiment, a 2.54 cm×81 cm Monel® reactor is used. About 500 ml of $FeCl_3$ catalyst supported on activated carbon was packed into the reactor. The reactor was heated to 150° C. under 1 liter/hr of nitrogen flow to dry the catalyst for 4 hours. Then, the reactor temperature is brought to 250° C. under the same nitrogen flow and 244fa is fed to the reactor at 1 g/min, and in the mean time the nitrogen flow is stopped. HFC-1234ze was found by using the in-line GC at the outlet of the reactor at 98% selectivity and 95% single pass conversion.

Example 6

The same experiment described in Example 5 is repeated, except that 245fa is used as feed. At the outlet of the reactor, 1234ze is found at 95% selectivity and 85% single pass conversion.

The principles, preferred embodiments, and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art, without departing from the spirit of the invention.

What is claimed is:

1. A dehydrohalogenation process for the preparation of fluoropropenes of the formula $CF_3CY=CX_NH_P$, wherein X and Y are independently hydrogen or a halogen selected from the group consisting of fluorine, chlorine, bromine and iodine; and N and P are independently integers equal to 0, 1, or 2, provided that (N+P)=2; comprising reacting a halopropane of the formula:

$$CF_3C(YR_1)C(X_NH_PR_2)$$

wherein $R_1$, $R_2$, X and Y are independently hydrogen or a halogen selected from the group consisting of fluorine, chlorine, bromine and iodine, provided that at least one of $R_1$, $R_2$, X and Y is a halogen and there is at least one hydrogen and one halogen on adjacent carbon atoms; with a caustic solution of at least one alkali metal or alkaline earth metal hydroxide in a non-aqueous, non-alcohol solvent for said alkali metal or alkaline earth metal hydroxide that is essentially miscible with said halopropane.

2. The process of claim 1 wherein the reactant comprises 1-chloro-1,3,3,3-tetrafluoropropane.

3. The process of claim 1 wherein the reactant comprises 1,1,1,3,3-pentafluoropropane.

4. The process of claim 1 wherein the reactant comprises both 1-chloro-1,3,3,3-tetrafluoropropane and 1,1,1,3,3-pentafluoropropane.

5. The process of claim 4 wherein said dehydrochlorination of 1-chloro-1,3,3,3-tetrafluoropropane and said dehydrofluorination of 1,1,1,3,3-pentafluoropropane are conducted simultaneously in the same reactor.

6. The process of claim 1 wherein said caustic solution comprises LiOH, NaOH, KOH, CaO, $Ca(OH)_2$, $CaCO_3$, lime stone or combinations thereof.

7. The process of claim 1, wherein said caustic solution solvent is selected from the group consisting of nitriles, ethers, esters, amides, ketones, sulfoxides, phosphates, carboxylates, and combinations of two or more of these.

8. The process of claim 1, wherein said caustic solution solvent comprises acetonitrile.

9. The process of claim 1, wherein said caustic solution solvent comprises diethyl ether.

10. The process of claim 1, wherein said caustic solution solvent comprises tetrahydrofuran.

11. The process of claim 1, wherein said caustic solution solvent comprises perfluorotetrahydrofuran.

12. The process of claim 1, wherein said caustic solution solvent comprises methyl acetate.

13. The process of claim 1, wherein said caustic solution solvent comprises ethyl acetate.

14. The process of claim 1 wherein the reaction is conducted at a temperature of from about 20° C. to about 150° C.

15. The process of claim 1 wherein the reaction is conducted at atmospheric pressure or under vacuum.

16. The process or claim 1 wherein the reaction is conducted at superatmospheric pressure.

17. The process of claim 1 wherein the caustic strength of said caustic solution is from about 2 wt % to about 100 wt %.

18. The process of claim 1, wherein the molar ratio of caustic to halopropane is about 1:1 to about 20:1.

19. A dehydrohalogenation process for the preparation of fluoropropenes of the formula $CF_3CY=CX_NH_p$, wherein X and Y are independently hydrogen or a halogen selected from the group consisting of fluorine, chlorine, bromine and iodine, and N and P are independently integers equal to 0, 1 or 2, provided that (N+P)=2; comprising heating to a temperature at which dehydrohalogenation by thermal decomposition occurs, a halopropene of the formula:

$$CF_3C(YR_1)C(X_NH_PR_2)$$

wherein $R_1$, $R_2$, X and Y are independently hydrogen or a halogen selected from the group consisting of fluorine, chlorine, bromine and iodine, provided that least one of $R_1$, $R_2$, X and Y is a halogen and there is at least one hydrogen and one halogen on adjacent carbon atoms.

20. The process of claim 19 wherein the reactant comprises 1-chloro-1,3,3,3-tetrafluoropropane.

21. The process of claim 19 wherein the reactant comprises 1,1,1,3,3-pentafluoropropane.

22. The process of claim 19 wherein the reactant comprises both 1-chloro-1,3,3,3-tetrafluoropropane and 1,1,1,3,3-pentafluoropropane.

23. The process of claim 22 wherein said dehydrochlorination of 1-chloro-1,3,3,3-tetrafluoropropane and said dehydrofluorination of 1,1,1,3,3-pentafluoropropane are conducted simultaneously in the same reactor.

24. The process of claim 19 wherein the reaction is conducted at a temperature of from about 30° C. to about 400° C.

25. The process of claim 19 wherein the reaction is conducted at a temperature of from about 50° C. to about 350° C.

26. The process of claim 19 wherein the reaction is conducted at a temperature of from about 75° C. to about 300° C.

27. The process of claim 19 wherein the reaction is conducted at atmospheric pressure or under vacuum.

28. The process or claim 19 wherein the reaction is conducted at superatmospheric pressure.

29. The process of claim 19 wherein said decomposing is conducted in the presence of a transition metal halide catalyst.

30. The process of claim 29 wherein said transition metal is selected from the group consisting of iron, nickel, cobalt, and combinations thereof.

31. The process of claim 29 wherein the catalyst is supported or bulk transition metal halides.

32. The process of claim 29 wherein said catalyst comprises supported or bulk $FeCl_2$, $FeCl_3$, $NiCl_2$ or $CoCl_2$.

* * * * *